(12) United States Patent
Huh

(10) Patent No.: US 9,024,646 B2
(45) Date of Patent: May 5, 2015

(54) CIRCUIT FOR MEASURING INSULATION RESISTANCE

(71) Applicant: SK Innovation Co., Ltd., Seoul (KR)

(72) Inventor: Geun Hoe Huh, Daejeon (KR)

(73) Assignee: SK Innovation Co., Ltd. (KR)

( * ) Notice: Subject to any disclaimer, the term of this patent is extended or adjusted under 35 U.S.C. 154(b) by 169 days.

(21) Appl. No.: 13/733,926

(22) Filed: Jan. 4, 2013

(65) Prior Publication Data

US 2013/0176042 A1 Jul. 11, 2013

(30) Foreign Application Priority Data

Jan. 5, 2012 (KR) .................. 10-2012-0001443

(51) Int. Cl.
*G01N 27/04* (2006.01)
*B60L 3/00* (2006.01)
*G01R 31/02* (2006.01)
*B60L 3/12* (2006.01)
*G01R 27/18* (2006.01)
*G01R 31/00* (2006.01)

(52) U.S. Cl.
CPC .............. *G01N 27/04* (2013.01); *B60L 3/0069* (2013.01); *G01R 27/18* (2013.01); *G01R 31/025* (2013.01); *G01R 31/007* (2013.01); *B60L 3/0046* (2013.01); *B60L 3/12* (2013.01)

(58) Field of Classification Search
None
See application file for complete search history.

(56) References Cited

U.S. PATENT DOCUMENTS

2010/0308841 A1* 12/2010 Karrer et al. .................. 324/551

FOREIGN PATENT DOCUMENTS

| JP | 06308185 | 11/1994 |
|---|---|---|
| KR | 1020090024573 | 3/2009 |

* cited by examiner

*Primary Examiner* — Melissa Koval
*Assistant Examiner* — Stephen G Armstrong
(74) *Attorney, Agent, or Firm* — Cantor Colburn LLP

(57) ABSTRACT

Provided is a circuit for measuring insulation resistance, including: a first operational amplifier that is connected with a positive terminal of a battery and a second operational amplifier; a second operational amplifier that is connected with a negative terminal of the battery and the first operational amplifier; a first switch that is connected between the positive terminal and a non-inverting terminal of the first operational amplifier; and a second switch that is connected between the negative terminal and an inverting terminal of the second operational amplifier, wherein the first operational amplifier and the second operational amplifier are connected with each other through a ground.

8 Claims, 4 Drawing Sheets

FIG. 1
*Prior Art*

| | Battery(-) to chassis GND isolation fault check | Battery(+) to chassis GND isolation fault check |
|---|---|---|
| Diagram | | |
| Switch S(+) | On | Off |
| Switch S(-) | Off | On |
| Switch St(+) | Off | Off |
| Switch St(-) | Off | Off |
| V(+) Voltage | $V(+) = \dfrac{R}{R_{iso} + R} V$ | N/A |
| V(-) Voltage | N/A | $V(-) = \dfrac{R}{R_{iso} + R} V$ |

CIRCUIT FOR MEASURING INSULATION RESISTANCE

CROSS-REFERENCE TO RELATED APPLICATIONS

This application claims priority under 35 U.S.C. §119 to Korean Patent Application No. 10-2012-0001443, filed on Jan. 5, 2012, in the Korean Intellectual Property Office, the disclosure of which is incorporated herein by reference in its entirety.

TECHNICAL FIELD

The present invention relates to a circuit for measuring insulation resistance, and more particularly, to a circuit for measuring insulation resistance capable of checking an isolation breakdown of a high voltage battery of a hybrid vehicle in real time.

BACKGROUND

FIG. 1 illustrates a ground fault detection circuit (GFD) that has been used in most of the battery management systems.

The ground fault detection circuit determines an isolation breakdown of a battery by forming a current path connected to a positive terminal of a battery, a ground, and a negative terminal thereof and measuring voltage applied to a resistor R.

That is, the ground fault detection circuit alternately opens and closes a switch S (+) and S (−) using voltage V applied to a high-voltage battery to measure the voltage applied to the resistor R and since an insulation resistance value RISO is reduced when a voltage of a predetermined level or more is applied to the resistor, determines that the isolation breakdown occurs.

Therefore, the ground fault detection circuit has a problem in that voltage applied to an operational amplifier may be changed according to a change in the voltage V of the battery even in the case of the same insulation resistance value RISO. Further, according to the circuit illustrated in FIG. 1, it is assumed that insulation resistor RISO− between the negative terminal of the battery and the ground of the vehicle has an infinite resistance value at the time of measuring insulation resistor RISO+ between the positive terminal of the battery and the ground of the vehicle, while the insulation resistor RISO+ between the positive terminal of the battery and the ground of the vehicle has an infinite resistance value at the time of measuring insulation resistor RISO− between the negative terminal of the battery and the ground of the vehicle. Therefore, there is a problem in that the ground fault detection circuit according to the related art cannot normally measure the isolation breakdown when the insulation of both of the positive terminal of the battery and the negative terminal are broken, that is, the values of both of the insulation resistor RISO+ between the positive terminal of the battery and the ground of the vehicle and the insulation resistor RISO− between the negative terminal of the battery and the ground of the vehicle are small.

Therefore, a need exists for a development of a circuit capable of determining the isolation breakdown without using the ground fault detection circuit forming the current path by connecting among the positive terminal of the battery, the ground, and the negative terminal of the battery.

RELATED ART DOCUMENT

Patent Document (Patent Document 1) Korean Patent Laid-Open Publication No. 2009-0024573

SUMMARY

An exemplary embodiment of the present invention is directed to providing a circuit for measuring insulation resistance capable of determining an isolation breakdown by directly connecting a specific power supply with a positive terminal or a negative terminal of a battery through a switch and directly sensing voltage applied to an insulation resistor.

In one general aspect, there is provided a circuit for measuring insulation resistance, including: a first operational amplifier that is connected with a positive terminal of a battery and a second operational amplifier; a second operational amplifier that is connected with a negative terminal of the battery and the first operational amplifier; a first switch that is connected between the positive terminal and a non-inverting terminal of the first operational amplifier; and a second switch that is connected between the negative terminal and an inverting terminal of the second operational amplifier, wherein the first operational amplifier and the second operational amplifier are connected with each other through a ground.

The first operational amplifier may sense voltage applied to an insulation resistor that is connected between the positive terminal and the ground and output the sensed voltage through an output terminal thereof.

The second operational amplifier may sense voltage applied to an insulation resistor that is connected between the negative terminal and the ground and output the sensed voltage through an output terminal thereof.

The first switch and the second switch may be periodically turned on/off using power generated within a management system circuit of the battery.

The battery may be a high voltage battery of a hybrid vehicle.

Other features and aspects will be apparent from the following detailed description, the drawings, and the claims.

BRIEF DESCRIPTION OF THE DRAWINGS

FIG. 1 is a circuit diagram illustrating a ground fault detection circuit (GFD) that is used in most of the battery management systems.

DETAILED DESCRIPTION OF EMBODIMENTS

Figure 2:
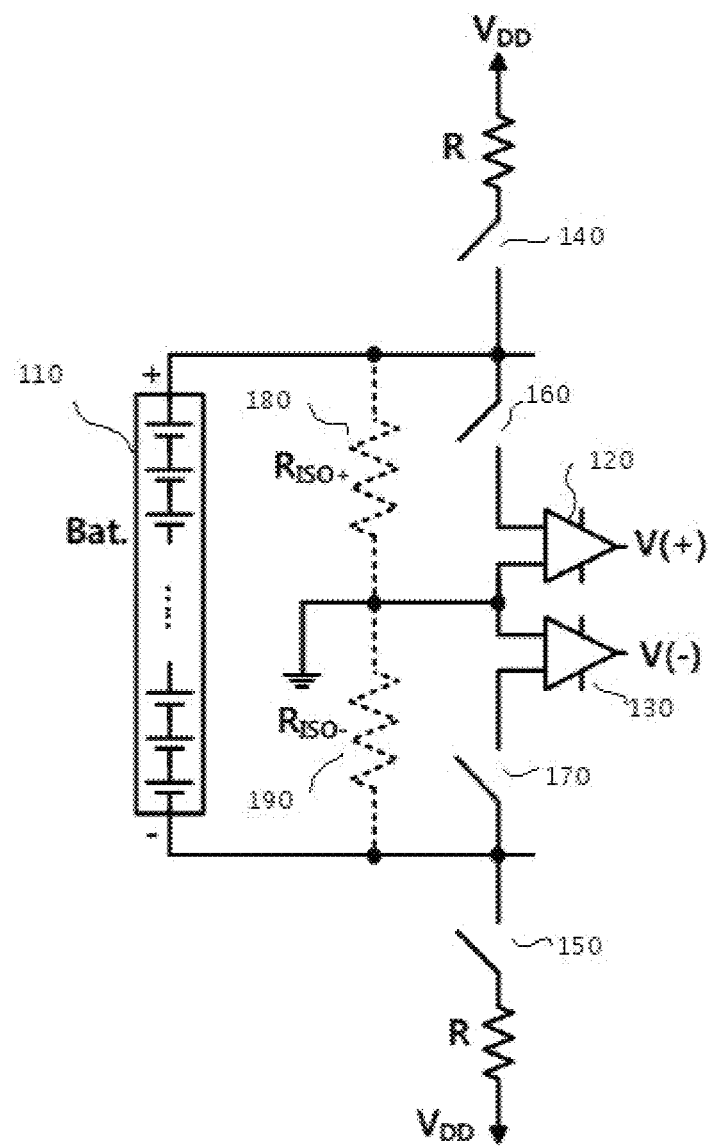
FIG. 2 is a circuit diagram illustrating a circuit for measuring insulation resistance according to an exemplary embodiment of the present invention.

Hereinafter, a circuit for measuring insulation resistance according to exemplary embodiments of the present invention will be described in detail with reference to the accompanying drawings. The following introduced drawings are provided by way of example so as to fully convey an idea of the present invention to a person skilled in the art to which the present invention pertains. Accordingly, the scope of the present invention is not restricted to the following description and accompanying drawings. In addition, throughout the specification, like reference numerals denotes like components.

Here, unless indicated otherwise, the terms used in the specification including technical and scientific terms have the same meaning as those that are usually understood by those who skilled in the art to which the present invention pertains, and detailed description of the known functions and constitutions that may obscure the gist of the present invention will be omitted.

FIG. 2 is a circuit diagram illustrating a configuration of a circuit for measuring insulation resistance according to an exemplary embodiment of the present invention.

As illustrated in FIG. 2, the circuit for measuring insulation resistance according to an exemplary embodiment of the present invention may include a battery 110, a first operational amplifier 120, a second operational amplifier 130, a first switch 140, a second switch 150, a third switch 160, a fourth switch 170, and the like.

The first operational amplifier 120 is connected with a positive terminal of a battery 110 and the second operational amplifier 130 and the second operational amplifier 130 is connected with a negative terminal of the battery 110 and the first operational amplifier 120.

The first switch 140 is connected between the positive terminal of the battery 110 and a non-inverting terminal of the first operational amplifier 120 and the second switch 150 is connected between the negative terminal of the battery 110 and an inverting terminal of the second operational amplifier 130.

The third switch 160 may be connected between the first switch 140 and the non-inverting terminal of the first operational amplifier 120.

The fourth switch 170 may be connected between the second switch 150 and the inverting terminal of the second operational amplifier 130.

As illustrated in FIG. 2, the first operational amplifier 120 and the second operational amplifier 130 may be connected with each other through a ground.

The first operational amplifier 120 senses voltage applied to an insulation resistor RISO+ 180 that is connected between the positive terminal of the battery 110 and the ground and outputs the sensed voltage through an output terminal thereof.

The second operational amplifier 130 senses voltage applied to an insulation resistor RISO− 190 that is connected between the negative terminal of the battery 110 and the ground and outputs the sensed voltage through an output terminal thereof.

In this configuration, the insulation resistors RISO+ and RISO− 180 and 190 are resistors shown by a dotted line in FIG. 2 and are not resistors connected with a real circuit but are virtual resistors that are generated by insulating the positive terminal and the negative terminal of the battery 110, respectively, from a ground of a vehicle.

The first switch 140 and the second switch 150 are periodically turned on/off using power generated within a management system circuit of the battery 110.

The circuit for measuring insulation resistance according to the exemplary embodiment of the present invention senses voltages V(+) and V(−) applied to the insulation resistors RISO+ and RISO− 180 and 190 while periodically turning on/off the first switch 140 and the second switch 150 to check an isolation breakdown. That is, the voltage V(+) applied to the insulation voltage RISO+ 180 is measured by turning on the first switch 140 and the third switch 160 and the voltage V(−) applied to the insulation resistor RISO− 190 is measured by turning on the second switch 150 and the fourth switch 170.

As described above, according to the exemplary embodiment of the present invention, the circuit for measuring insulation resistance can normally sense both of the cases in which both of insulation resistor between a positive terminal of the battery and a ground of a vehicle and insulation resistor between a negative terminal of the battery and the ground of the vehicle are broken, without additional circuit cost and accurately sense the isolation breakdown regardless of a change in a charged and discharged amount of the battery.

Further, the circuits for measuring insulation resistance according to the exemplary embodiment of the present invention may be each disposed across a relay, that is, at a battery side and an inverter side to determine whether the insulation resistor is broken in front of the relay or behind thereof.

Figure 3:
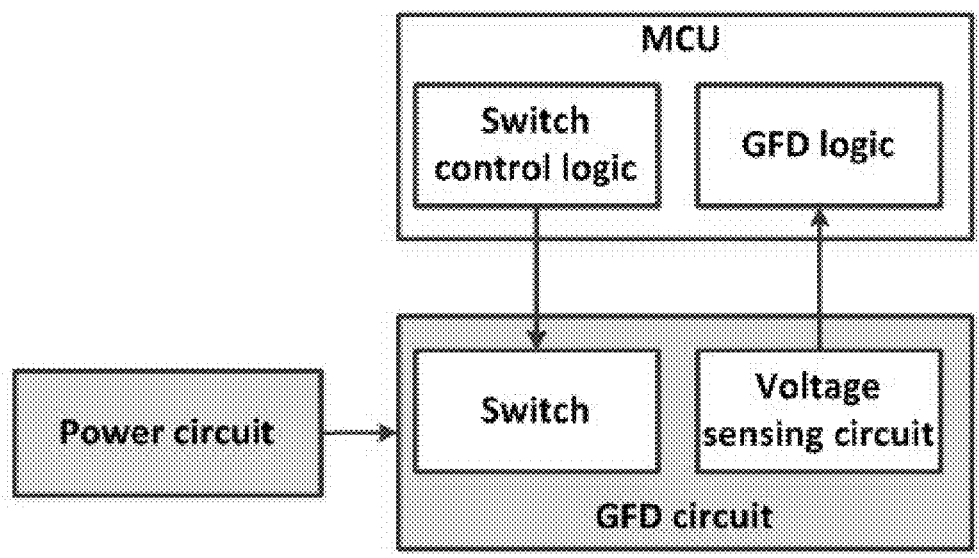
FIG. 3 is a schematic block diagram for using the circuit for measuring insulation resistance according to the exemplary embodiment of the present invention.

FIG. 3 is a schematic block diagram for using the circuit for measuring insulation resistance according to the exemplary embodiment of the present invention. As illustrated in FIG. 3, the circuit for measuring insulation resistance according to the exemplary embodiment of the present invention may be largely divided into a switch and a voltage sensing circuit. In this configuration, the switch is the first switch 140, the second switch 150, the third switch 160, and the fourth switch 170 and the voltage sensing circuit includes the first operational amplifier 120 and the second operational amplifier 130. A power circuit illustrated in FIG. 3 is to drive the circuit for measuring insulation resistance and includes power supply voltage represented by VDD in FIG. 2. As described above, a micro controller unit (MCU) illustrated in FIG. 3 controls an operation of the circuit for measuring insulation resistance to determine the isolation breakdown.

Figure 4:
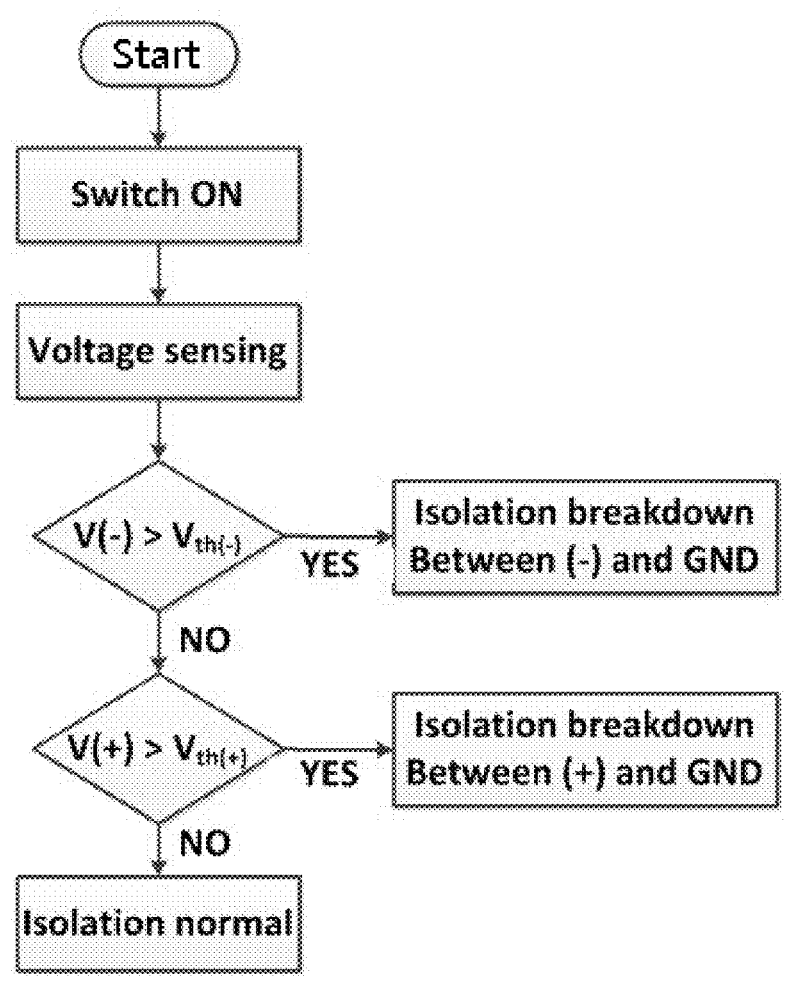
FIG. 4 is a flow chart illustrating an operation of the circuit for measuring insulation resistance according to the exemplary embodiment of the present invention.

FIG. 4 is a flow chart illustrating an operation of the circuit for measuring insulation resistance according to the exemplary embodiment of the present invention. As illustrated in FIG. 4, the circuit for measuring insulation resistance according to the exemplary embodiment of the present invention measures the voltage applied to the insulation resistor that is connected between the positive terminal of the battery and the ground or the voltage applied to the insulation resistor that is connected between the negative terminal of the battery and the ground by operating the switch of FIG. 3. The circuit for measuring insulation resistance according to the exemplary embodiment of the present invention determines the isolation breakdown based on the measured voltage.

According to the exemplary embodiment of the present invention, the circuit for measuring insulation resistance can normally sense both of the cases in which both of the insulation resistor between the positive terminal of the battery and the ground of the vehicle and the insulation resistor between the negative terminal of the battery and the ground of the vehicle are broken, without the additional circuit cost, and accurately sense the isolation breakdown regardless of the change in the charged and discharged amount of the battery.

As described above, the present invention is described with reference to specific matters such as the detailed components and the limited exemplary embodiments, but is provided to help a general understanding of the present invention. Therefore, the present invention is not limited to the above exemplary embodiments and can be variously changed and modified from the description by a person skilled in the art to which the present invention pertain.

The spirit of the present invention is defined by the appended claims rather than by the description preceding them, and all changes and modifications that fall within metes and bounds of the claims, or equivalents of such metes and bounds are therefore intended to be embraced by the range of the spirit of the present invention.

What is claimed is:

1. A system for measuring insulation resistance, comprising:
   a first operational amplifier that is connected with (i) a positive terminal of a battery without having any resistor between the first operational amplifier and the positive terminal and (ii) a second operational amplifier through a ground;
   the second operational amplifier that is connected with (i) a negative terminal of the battery without having any resistor between the first operational amplifier and the positive terminal and (ii) the first operational amplifier through the ground;
   a first switch that is connected between the positive terminal and a non-inverting terminal of the first operational amplifier;
   a second switch that is connected between the negative terminal and an inverting terminal of the second operational amplifier; and
   a controller configured to determine insulation breakdown between the positive terminal and the ground by closing the first switch.

2. The system of claim 1, wherein the first operational amplifier senses voltage applied to an insulation resistor that is connected between the positive terminal and the ground and outputs the sensed voltage through an output terminal thereof.

3. The system of claim 1, wherein the second operational amplifier senses voltage applied to an insulation resistor that is connected between the negative terminal and the ground and outputs the sensed voltage through an output terminal thereof.

4. The system of claim 1, wherein the first switch and the second switch are periodically turned on/off using power generated within a management system circuit of the battery.

5. The system of claim 1, wherein the battery is a high voltage battery of a hybrid vehicle.

6. The system of claim 1, wherein the controller is further configured to determine insulation breakdown between the negative terminal and the ground by closing the second switch.

7. The system of claim 1, wherein the non-inverting terminal of the first operational amplifier is not connected through a resistor to an inverting terminal of the first operational amplifier.

8. The system of claim 1, wherein the inverting terminal of the second operational amplifier is not connected through a resistor to a non-inverting terminal of the first operational amplifier.

* * * * *